US007019145B2

(12) United States Patent
Buisine et al.

(10) Patent No.: US 7,019,145 B2
(45) Date of Patent: Mar. 28, 2006

(54) METHOD FOR PREPARING METALLIC CARBENE-BASED CATALYSTS FOR HYDROSILYLATION OF UNSATURATED COMPOUNDS AND RESULTING CATALYSTS

(75) Inventors: Olivier Buisine, Lyons (FR); Istvan Marko, Grez-Doiceau (BE); Sebastien Sterin, Lyons (FR)

(73) Assignee: Rhodia Chimie, Boulogne-Billancourt Cedex (FR)

( * ) Notice: Subject to any disclaimer, the term of this patent is extended or adjusted under 35 U.S.C. 154(b) by 36 days.

(21) Appl. No.: 10/479,808

(22) PCT Filed: Jun. 4, 2002

(86) PCT No.: PCT/FR02/01896

§ 371 (c)(1), (2), (4) Date: May 25, 2004

(87) PCT Pub. No.: WO02/098888

PCT Pub. Date: Dec. 12, 2002

(65) Prior Publication Data

US 2004/0198996 A1 Oct. 7, 2004

(30) Foreign Application Priority Data

Jun. 7, 2001 (FR) .................................. 01 07475

(51) Int. Cl.

*C07F 15/00* (2006.01)
*C07F 7/08* (2006.01)
*B01J 31/00* (2006.01)

(52) U.S. Cl. ...................... 548/101; 556/479; 556/474; 556/140; 556/136; 556/12; 502/152; 502/158

(58) Field of Classification Search .................. 556/12, 556/136, 140, 474, 478; 548/101; 502/152, 502/158

See application file for complete search history.

(56) References Cited

U.S. PATENT DOCUMENTS 2,823,218 A 2/1958 Hook
2,970,150 A 1/1961 Bailey
3,775,452 A 11/1973 Karstedt
5,359,113 A 10/1994 Bank

OTHER PUBLICATIONS

Enders et al., "*Diastereoselective Systhesis of Chiral (triazolinylidene)rhodium Complexes Containing an Axis of Chirality*," Eur. J. Inorg. Chem. No. 7, 1998, pp. 913-919.

*Primary Examiner*—Porfirio Nazario-Gonzalez
(74) *Attorney, Agent, or Firm*—Buchanan Ingersoll, P.C.

(57) ABSTRACT

The invention concerns an improved method for preparing catalysts for hydrosilylation reactions of compounds with ethylene or acetylene unsaturation (for example olefins or acetylene derivatives), in particular but not exclusively those involving polyorganosiloxanes (POS) bearing Si—H units and POS bearing Si-(ethylene or acetylene unsaturation) units. Said preparation corresponds to the following synthesis (I), wherein: A=B=carbon: $T_1$, $T_2$=cyclohexyl, t-butyl or methyl; $T_3$, $T_4$=H; DVTMS=divinyltetramethylsiloxane; t-BuOK=potassium tert-butylate; T.A=room temperature. The invention is characterised in that it consists in carrying out said synthesis in a single step by bringing together salt (III) above, Karstedt (IV) in the presence of a solvent (V) (THF) and a base (VI) (t-BuOK) at room temperature.

(I)

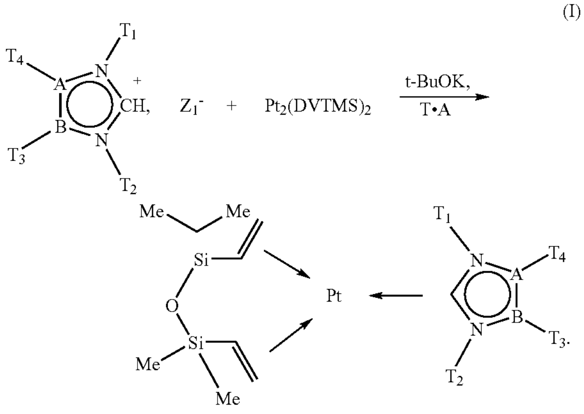

11 Claims, No Drawings

METHOD FOR PREPARING METALLIC CARBENE-BASED CATALYSTS FOR HYDROSILYLATION OF UNSATURATED COMPOUNDS AND RESULTING CATALYSTS

The invention relates to the preparation of catalysts for hydrosilylation reactions and especially for the hydrosilylation of ethylenically and/or acetylenically unsaturated compounds (for example olefins or acetylenic derivatives), in particular, but not limited to, those involving polyorganosiloxanes (POS) bearing Si—H units and POSs bearing Si-(ethylenic or acetylenic unsaturation) units.

Conventionally, hydrosilylation catalysts are platinum catalysts (U.S. Pat. No. 2,823,218, U.S. Pat. No. 2,970,150). In practice, to date, the majority of industrial hydrosilylation reactions are catalyzed with Karstedt solution, which consists of complexes of platinum in oxidation state 0. The ideal general formula of the Karstedt complex is $Pt_2$(tetramethyldivinylsiloxane)$_3$:

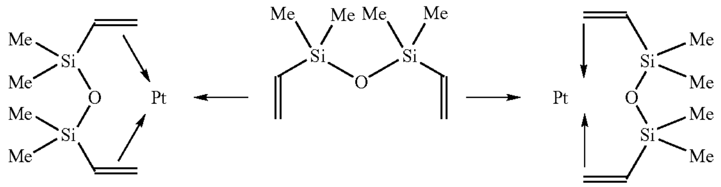

in which Me represents methyl.

The Karstedt complex is prepared by placing 1,3-divinyltetramethyldisiloxane in contact with chloroplatinic acid ($H_2PtCl_6$), in the presence of $NaHCO_3$ and an aqueous-alcoholic solvent (isopropanol).

This common catalyst and its production are described in patent U.S. Pat. No. 3,775,452.

The unpublished patent application FR 99/15432 of Dec. 07, 1999 discloses metallic complexes that are useful as hydrosilylation catalysts, of formula:

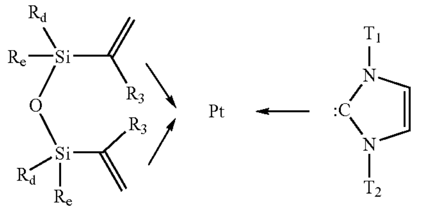

in which:

$R_3$ represents a hydrogen atom; a $(C_1$–$C_8)$alkyl group; or a $(C_3$–$C_8)$cycloalkyl group optionally substituted with $(C_1$–$C_4)$alkyl;

$T_1$ and $T_2$ are identical and represent $(C_1$–$C_8)$alkyl or $(C_3$–$C_8)$cycloalkyl;

$R_d$ and $R_e$ are identical and represent $(C_1$–$C_8)$alkyl or $(C_3$–$C_8)$cycloalkyl, (preferably, $T_1$=$T_2$=$R_d$=$R_e$=methyl).

These Pt/carbene metallic complexes are obtained according to a two-step methodology illustrated by the following example:

1. Preparation of the Carbene:

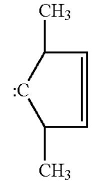

2. Preparation of the Platinum Complex of Formula:

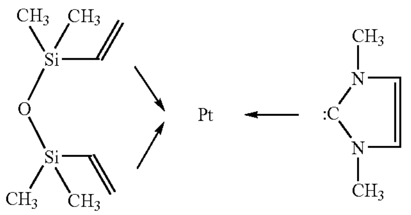

In step 1, a reaction medium is used comprising a carbene precursor: for example, 1,3-dimethylimidazolinium iodide, a solvent system comprising THF and ammonia, and a base: NaH. After deprotonation and evaporation of the ammonia, a solution of carbene in THF is obtained.

In step 2, this carbene solution is mixed with a solution of platinic Karstedt complex. After reaction and various filtration, purification, concentration, washing and precipitation steps, a solid Pt/carbene complex is obtained.

This preparation method would profit from being simplified and optimized, especially as regard the yield and the production efficiency, with a view to an industrial application.

U.S. Pat. No. 5,728,839 also discloses the two-step preparation of metallic/carbene complexes, from imidazolium, benzimidazolium, triazolium, tetrazolium or pyrazolium salts (for example iodide). The carbene is obtained in a first stage by placing the imidazolium, benzimidazolium, triazolium, tetrazolium or pyrazolium salt in contact with a deprotonating base, NaH, dissolved in THF. In a second stage, the metallic (rhodium) complex is obtained by exchange between the carbene and a metal/cycloolefin complex (for example a di(μ-chloro)bis($\eta^4$-1,5-cyclooctadiene) dirhodium).

With such a state of the art, one of the essential objectives of the invention is to propose an improved and efficient process for preparing metallic complexes of formula (I):

I

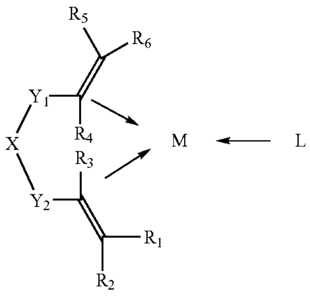

Another essential objective of the invention is to propose a process for preparing metallic complexes of formula I, which is improved compared with the process described in the prior unpublished patent application FR 99/15432 in terms of simplification of methodology, increase in yield and reduction in cost.

Another essential objective of the invention is to propose an improved process for preparing metallic complexes of formula I used as hydrosilylation catalysts, these catalysts needing to be stable in the reaction medium, so as:

- to product a selective catalytic activity of a high qualitative and quantitative level, and
- to limit the formation:
  - of undesirable side products resulting from isomerization reactions of the olefinic double bond and/or of hydrogenation reactions
  - and/or of side products that are the origin of entirely undesired colorations.

Another essential objective of the invention is to propose a hydrosilylation process and in particular for the hydrosilylation of ethylenically and/or acetylenically unsaturated compounds, in the presence of a catalyst comprising the metallic complex obtained by the abovetargeted process.

These objectives, among others, are achieved by the present invention, which relates firstly to a process for preparing metallic complexes of formula (I):

I

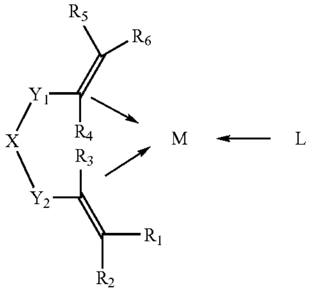

in which:

M represents a metal chosen from the metals of group 8 of the Periodic Table as published in the Handbook of Chemistry and Physics, 65th Edition, 1984–1985;

X represents O, $NR_a$ or $CR_fR_g$;

$Y_1$ and $Y_2$ represent, independently of each other, $CR_bR_c$ or $SiR_dR_e$;

$R_1$, $R_2$, $R_3$, $R_4$, $R_5$, $R_6$, $R_a$, $R_b$ and $R_c$, which may be identical or different, are chosen from a hydrogen atom; an alkyl group; an acyl group; an aryl group optionally substituted with alkyl; a cycloalkyl group optionally substituted with alkyl; and an arylalkyl group in which the aryl portion is optionally substituted with alkyl;

$R_d$ and $R_e$ are independently chosen from alkyl; aryl optionally substituted with alkyl; cycloalkyl optionally substituted with alkyl; and arylalkyl in which the aryl portion is optionally substituted with alkyl; or alternatively when $Y_1$ and $Y_2$ independently represent $SiR_dR_e$, two groups $R_d$ linked to two separate silicon atoms together form a chain of formula:

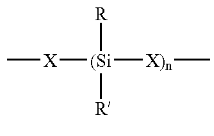

in which n is an integer from 1 to 3; X is as defined above; R and R', which may be identical or different, take any of the meanings given above for $R_e$, it being understood that, when n is 2 or 3, only one silicon atom of said chain may be substituted with one or two alkenyl or alkynyl groups; or alternatively when $Y_1$ and $Y_2$ independently represent $SiR_d R_e$, two groups $R_d$ linked to separate silicon atoms together form a saturated hydrocarbon-based chain, the two groups $R_d$ together with said silicon atoms and X forming a 6- to 10-membered ring; or alternatively when $Y_1$ and $Y_2$ independently represent $CR_bR_c$, two groups $R_b$ linked to separate carbon atoms together form a saturated hydrocarbon-based chain, the two groups $R_b$ together with the carbon atoms that bear them and X form a 6- to 10-membered ring; and $R_f$ and $R_g$ represent, independently of each other, a hydrogen atom; an alkyl group; an acyl group; an aryl group optionally substituted with alkyl; a cycloalkyl group optionally substituted with alkyl; an arylalkyl group in which the aryl portion is optionally substituted with alkyl; a halogen atom; an alkenyl group; an alkynyl group; or a group $SiG_1G_2G_3$ in which $G_1$, $G_2$ and $G_3$ are, independently of each other, alkyl; alkoxy; aryl optionally substituted with alkyl or alkoxy; or arylalkyl in which the aryl portion is optionally substituted with alkyl or alkoxy; L represents a carbene of formula (II):

(II)

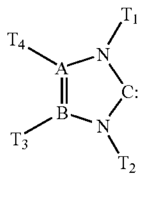

in which:

A and B independently represent C or N, it being understood that when A represents N, then $T_4$ represents nothing, and when B represents N, then $T_3$ represents nothing;

$T_3$ and $T_4$ independently represent a hydrogen atom; an alkyl group; a cycloalkyl group optionally substituted with alkyl or alkoxy; an aryl group optionally substituted with alkyl or alkoxy; an alkenyl group; an alkynyl group; or an arylalkyl group in which the aryl portion is optionally substituted with alkyl or alkoxy; or alternatively $T_3$ and $T_4$ may form, together with A and B when these each represent a carbon atom, an aryl;

$T_1$ and $T_2$ independently represent an alkyl group; an alkyl group optionally substituted with alkyl; a perfluoroalkyl group or an alkyl group optionally substituted with a perfluoroalkyl group; a cycloalkyl group optionally substituted with alkyl or alkoxy; an aryl group optionally substituted with alkyl or alkoxy; an alkenyl group; an alkynyl group; or an arylalkyl group in which the aryl portion is optionally substituted with alkyl or alkoxy; or alternatively $T_1$ and $T_2$ independently represent a monovalent radical of formula (V) below:

$$—V_1—V_2 \qquad (V)$$

in which:

$V_1$ is a divalent hydrocarbon-based radical, preferably an optionally substituted linear or branched $C_1$–$C_{10}$ alkylene, $V_2$ is a monovalent radical chosen from the following group of substituents:

alkoxy, —$OR^{\nu}$ with $R^{\nu}$ corresponding to hydrogen, alkyl or aryl amine, preferably $N(R^{\nu})_2$ with $R^{\nu}$ corresponding to hydrogen, alkyl or aryl, or alternatively $T_1$ and $T_2$ independently represent a monovalent radical of formula (W) below:

$$—W_1\text{-}\omega\text{-}W_2 \qquad (W)$$

in which:

$W_1$ is a divalent hydrocarbon-based radical, preferably an optionally substituted linear or branched $C_1$–$C_{10}$ alkylene, ω represents:

$$—R^{\alpha}C{=}CR^{\alpha}—$$

with $R^{\alpha}$ corresponding to H or alkyl or $$—C{\equiv}C—$$

$W_2$ is a monovalent radical chosen from the following group of substituents;

$R^{\beta}$=alkyl, H;

Si-alkyl, Si-alkenyl or Si-alkynyl, preferably Si-(alkyl)$_3$;

alcohol, preferably —$C(R^{\epsilon})_2OH$ with $R^{\epsilon}$=H or alkyl;

ketone, preferably

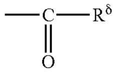

with $R^{\delta}$=alkyl; alkenyl, alkynyl;

carboxyl, preferably

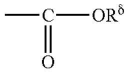

with $R^{\delta}$=alkyl; alkenyl, alkynyl;

amide, preferably

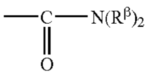

with $R^{\beta}$=H, alkyl; alkenyl, alkynyl;

acyl, preferably

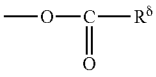

with $R^{\delta}$=alkyl; alkenyl, alkynyl;

or alternatively the substituents $T_1$, $T_2$, $T_3$ and $T_4$ can form in pairs, when they are located on two adjacent ring members in formula II, a saturated or unsaturated hydrocarbon-based chain.

This process consists essentially in placing in contact:

at least one salt of formula (III):

(III)

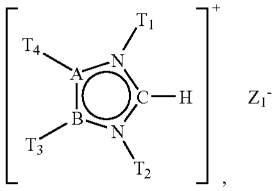

in which:

A, B, $T_1$, $T_2$, $T_3$ and $T_4$ are as defined above;

$Z_1$, independently represents an anion derived from a Brönsted acid (protic acid) preferably chosen from the group comprising:

carboxylic acids of formula Go-COOH in which Go represents an alkyl, and advantageously a $C_1$–$C_{22}$ alkyl; an aryl, advantageously a $C_6$–$C_{18}$ aryl optionally substituted with one or more $C_1$–$C_6$ alkyls;

sulfonic acids of formula Go-$SO_3H$ in which Go is as defined above;

phosphoric acids of formula Go-$PO_3H$ in which Go is as defined above;

the following mineral acids: HF, HCl, HBr, HI, $H_2SO_4$, $H_3PO_4$, $HClO_4$ and $HBF_4$ taken individually or in combination;

and mixtures thereof;

at least one precursor complex (IV) selected from the group of suitable complexes comprising the complexes of formula:

$$Pt_2[ViMe_2Si—O—SiMe_2Vi]_3 \text{ (Karstedt complex)}$$

in which Vi represents a vinyl radical;

and more generally the complexes of formula:

$$M_2[R_5R_6C{=}CR_4—Y_1—X—Y_2—CR_3{=}CR_1R_2]_3$$

in which M, $R_5$, $R_6$, $R_4$, $R_3$, $R_1$, $R_2$, $Y_1$, X and $Y_2$ are as defined above, for instance: $M_2[CR_5R_6{=}CR_4—SiRdRe—O—SiR_dR_e—CR_3{=}CR_1R_2]_3$, it being understood that M, $R_1$, $R_2$, $R_3$, $R_4$, $R_5$, $R_6$, $R_d$ and $R_e$ are as defined above;

at least one solvent (V), and at least one base (VI).

One of the essential characteristics of the process according to the invention is therefore to allow for the formation of the metal/carbene complex in a single step.

The procedure is thus greatly simplified. This advantage is all the more interesting since it is accompanied by an improvement in the yield and a reduction in the cost price, without, however, affecting the application properties of the metal complexes obtained. Specifically, they are selective, efficient and stable hydrosilylation catalysts that produce few isomerization and coloration side reactions.

The metallic complexes with which the process according to the invention is concerned are defined below.

The metals of group 8 represented by M are, for example, palladium, platinum or nickel in oxidation state 0. In practice, M represents platinum in oxidation state 0.

The term "alkyl" denotes a saturated, linear or branched hydrocarbon-based chain, which is optionally substituted (e.g. with one or more alkyls), preferably of 1 to 10 carbon atoms, for example 1 to 8 carbon atoms and better still 1 to 7 carbon atoms.

Examples of alkyl groups are especially methyl, ethyl, isopropyl, n-propyl, tert-butyl, isobutyl, n-butyl, n-pentyl, isoamyl and 1,1-dimethylpropyl.

The alkyl portion of the alkoxy radical is as defined above.

The perfluoroalkyl radical or alkyl radical optionally substituted with a perfluoroalkyl group preferably has the formula:

$$—(CH_2)_p—C_qF_{2q+1}$$

in which p represents 0, 1, 2, 3 or 4; q is an integer from 1 to 10; and $C_qF_{2q+1}$ is linear or branched. Preferred examples of this radical are:

$$—(CH_2)_2—(CF_2)_5—CF_3 \text{ and } —(CF_2)_7—CF_3.$$

The term "aryl" denotes a monocyclic or polycyclic and preferably monocyclic or bicyclic, aromatic hydrocarbon-based group containing from 6 to 18 carbon atoms. It should be understood that, in the context of the invention, the term "polycyclic aromatic radical" means a radical containing two or more aromatic nuclei, which are fused (ortho-fused or ortho- and peri-fused) together, i.e. having, in pairs, at least two carbons in common.

Said aromatic hydrocarbon-based group ("aryl") is optionally substituted, for example, with one or more $C_1$–$C_3$ alkyls, one or more halohydrocarbon radicals (e.g. $CF_3$), one or more alkoxy (e.g. $CH_3O$) or one or more hydrocarbon based radicals comprising one or more ketone units (e.g. $CH_3CO—$).

Examples of aryls that may be mentioned include phenyl, naphthyl, anthryl and phenanthryl radicals.

The term "arylalkyl" denotes an alkyl group as defined above, substituted with one or more aryl groups on its hydrocarbon-based chain, the aryl group being as defined above. Examples of these are benzyl and triphenylmethyl.

The term "acyl" means a group $R_o$—CO— in which $R_o$ represents alkyl as defined above; or a group Ar—CO— in which Ar represents an aryl group as defined above, or alternatively an arylalkyl group in which aryl and alkyl are as defined above and in which the aryl portion is optionally substituted, e.g. with alkyl.

The term "cycloalkyl" means a monocyclic or polycyclic, preferably monocyclic or bicyclic, saturated hydrocarbon-based radical preferably containing from 3 to 10 and better still from 3 to 8 carbon atoms. The term "saturated polycyclic hydrocarbon-based radical" means a radical containing two or more cyclic nuclei attached together via σ bonds and/or fused in pairs.

Examples of polycyclic cycloalkyl groups are adamantane and norbornane.

Examples of monocyclic cycloalkyl groups are cyclopropyl, cyclobutyl, cyclopentyl, cyclohexyl, cycloheptyl and cyclooctyl.

The term "alkenyl" means a linear or branched, substituted or unsubstituted, unsaturated hydrocarbon-based chain containing at least one olefinic double bond, and more preferably only one double bond. The alkenyl group preferably contains from 2 to 8 and better still from 2 to 6 carbon atoms. This hydrocarbon-based chain optionally comprises at least one hetero atom such as O, N or S.

Preferred examples of alkenyl groups are allyl and homoallyl groups.

According to the invention, the term "alkynyl" means a linear or branched, substituted or unsubstituted, unsaturated hydrocarbon-based chain containing at least one acetylenic triple bond, and more preferably only one triple bond. The alkynyl group preferably contains from 2 to 8 carbon atoms and better still from 2 to 6 carbon atoms. Examples that may be mentioned include the acetylenyl group and the propargyl group. This hydrocarbon-based chain optionally comprises at least one hetero atom such as O, N or S.

The expression "represents nothing" means that the substituents $—T_3$, or $—T_4$, respectively, are not present. Specifically, in formula (II), the nitrogen atom is trivalent, such that when A or B represents N, the nitrogen atom cannot contain an additional substituent.

The carbenes of formula (II) may contain at least two fused nuclei, i.e. at least two substituents from $T_1$, $T_2$, $T_3$ and $T_4$, located on two adjacent ring members, together form a saturated or unsaturated hydrocarbon-based chain preferably containing from 3 to 6 carbon atoms. The expression "saturated or unsaturated hydrocarbon-based chain" means a linear or branched hydrocarbon-based chain, possibly containing one or more unsaturations of olefinic double bond type or of acetylenic triple bond type.

When the carbenes (II) contain fused nuclei, they thus correspond to one of the formulae below, in which (alk) represents a saturated or unsaturated hydrocarbon-based chain:

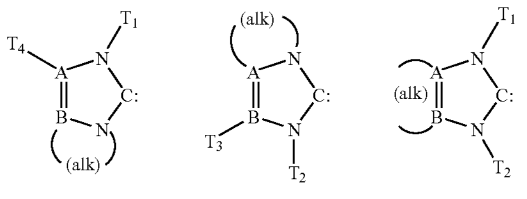

However, it should be understood that the carbenes II may contain more than two fused nuclei.

The complexes that are preferably prepared by the process according to the invention are those in which $Y_1$ and $Y_2$ either both represent $CR_bR_c$, or both represent $SiR_dR_e$, such that said complexes have either the formula (I.1) or the formula (I.2):

I.1

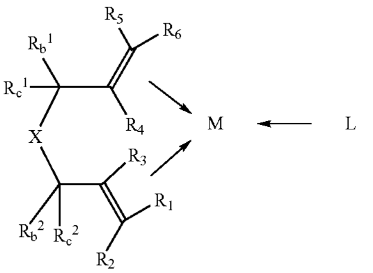

I.2

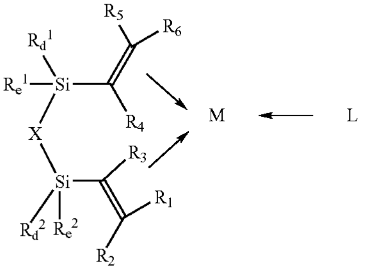

in which $R_b^1$ and $R_c^1$ are the substituents $R_b$ and $R_c$ of $Y_1$ in formula (I.1);

$R_b^2$ and $R_c^2$ are the substituents $R_b$ and $R_c$ of $Y_2$ in formula (I.2);

$R_d^1$ and $R_e^1$ are the substituents $R_b$ and $R_e$ of $Y_1$ in formula (I.1);

$R_d^2$ and $R_e^2$ are the substituents $R_d$ and $R_e$ of $Y_2$ in formula (I.2).

Thus, $R_b^1$ may be identical to or different than $R_b^2$; $R_c^1$ may be identical to or different than $R_c^2$; $R_d^1$ may be identical to or different than $R_d^2$; and $R_e^1$ may be identical to or different than $R_e^2$.

In practice:

$R_b^1=R_b^2$; $R_c^1=R_c^2$; $R_d^1=R_d^2$; and $R_e^1=R_e^2$.

$R_3=R_4$; $R_5=R_2$; and $R_1=R_6$.

According to one variant, $R_d^1$ and $R_d^2$ together form:

(a) either a chain:

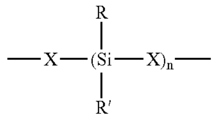

in which n is an integer from 1 to 3; X is as defined above; and R and R', which may be identical or different, take any of the meanings given above for $R_e$, it being understood that, when n is 2 or 3, only one silicon atom of said chain may be substituted with one or two alkenyl or alkynyl groups;

(b) or a saturated hydrocarbon-based chain, such that the two substituents $R_d$, together with the two silicon atoms that bear them and X, form a 6- to 10-membered ring and preferably a 6- to 8-membered ring.

When $R_d^1$ and $R_d^2$ form the chain (a), it is preferable for n to be 1 or 2 (better still, n is 1) and for $R=R_e$, the two groups $R_e$ borne by the two silicon atoms being identical. In this case, $R_e$ preferably represents alkyl, for example methyl. Better still, in these compounds, R' represents $-CR_3=CR_1R_2$ and $R_1=R_6$; $R_5=R_2$; and $R_3=R_4$.

When $R_d^1$ and $R_d^2$ form the chain (b), it is preferable for the two groups $R_d$, together with the two silicon atoms and the group X, to form an 8-membered ring. In this case, it is preferable for $R_e^1$ to be identical to $R_e^2$. These compounds have the general formula:

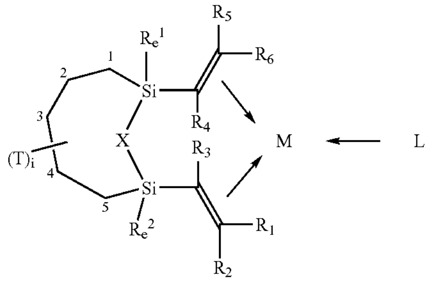

in which T represents alkyl and i is an integer between 0 and 5, T being located on one or more of the ring members 1, 2, 3, 4 and 5 of the above formula.

Similarly, when $Y_1$ and $Y_2$ represent $CR_bR_c$, the two groups $R_b$ linked to different carbon atoms may together form a saturated hydrocarbon-based chain (c), such that the two groups $R_b$, together with the carbons that bear them and X, form a 6- to 10-membered ring. Preferably, the ring formed is an 8-membered ring, in which case the metallic complex corresponds to the formula:

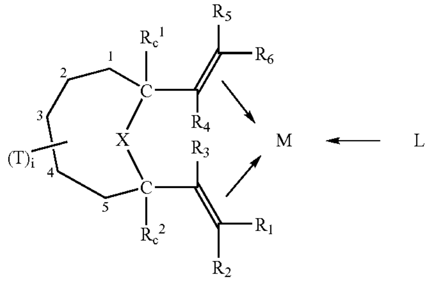

in which T represents alkyl; i is an integer between 0 and 5, T being located on one or more of the ring members 1, 2, 3, 4 and 5 of the above formula.

Two groups $R_d$ linked to two different silicon atoms can form a chain of formula:

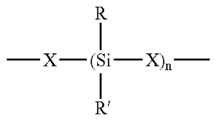

When this is the case, it is preferable for X to represent O in the compounds of the invention. These preferred compounds have the general formula:

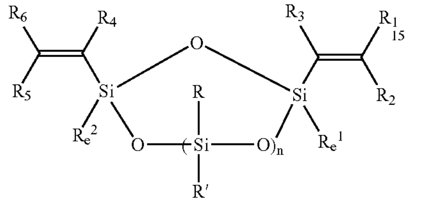

Among these compounds, it is preferable that $R_e^1 = R_e^2$ Advantageously, $R_e^1 = R_e^2$ represents alkyl (for example methyl).

Preferably, n is 1 or 2 and $R = R_e^1$, it being understood that when n is 2, only one silicon atom of the chain O—(SiRR'—O)$_n$— can be substituted with one or two alkenyl or alkynyl groups. Better still, $R' = -CR_3 = CR_1R_2$ and $R_1 = R_6$; $R_2 = R_5$ and $R_3 = R_4$.

When $R_f$ and/or $R_g$ represents $SiG_1G_2G_3$, it is preferable for $R_f$ and/or $R_g$ to be trialkylsilyl, for example $SiG_1G_2G_3$ in which $G_1 = G_2 = G_3$=alkyl.

Subgroups of the metallic complexes of the invention consist of complexes for which:

X=O; $Y_1$ and $Y_2$ independently represent $SiR_dR_e$; or

X=$NR_a$; $Y_1$ and $Y_2$ independently represent $CR_bR_c$; or

X=$NR_a$; $Y_1$ and $Y_2$ independently represent $SiR_dR_e$; or

X=$CR_fR_g$; $Y_1$ and $Y_2$ independently represent $CR_bR_c$; or

X=$CR_fR_g$; $Y_1$ and $Y_2$ independently represent $SiR_dR_e$.

Among these metallic complexes of formula (I) that are preferred are those for which:

when X represents O, $Y_1$ and $Y_2$ independently represent $SiR_dR_e$; or when X represents $NR_a$, $Y_1$ and $Y_2$ independently represent $CR_bR_c$; or when X represents $CR_fR_g$, $Y_1$ and $Y_2$ independently represent $CR_bR_c$.

In practice, X represents O and $Y_1$ and $Y_2$ independently represent $SiR_dR_e$ in the metallic complex of formula (I). In the context of the invention, the expression "independently represent" means that the designated substituents are either identical or different.

For example, $R_1$, $R_2$, $R_5$ and $R_6$ are hydrogen atoms.

Preferred meanings of $R_3$ and $R_4$ are especially a hydrogen atom; an alkyl group; an aryl group optionally substituted with alkyl; and a cycloalkyl group optionally substituted with alkyl. Among these preferred meanings it is particularly advantageous for $R_3$ and $R_4$, together, to represent a hydrogen atom; $(C_3$–$C_8)$cycloalkyl or $(C_1$–$C_8)$alkyl.

For example, the diolefinic ligand of the complex of formula (I) is symmetrical, i.e. $R_5 = R_2$; $R_6 = R_1$; $R_3 = R_4$ and the two groups $Y_1$ and $Y_2$ are either strictly identical to each other, or $Y_1$ represents $CR_b^1R_c$ and $Y_2 = CR_b^2R_c$ in which $R_b^1$ and $R_b^2$ together form a symmetrical chain, or alternatively $Y_1 = SiR_d^1R_e$ and $Y_2 = SiR_d^2R_e$ in which $R_d^1$ and $R_d^2$ together form a symmetrical chain.

A preferred group of complexes according to the invention consists of the complexes of formula (I) in which L represents a carbene of formula (II). Preferably, A and B in the formula (II) both represent a carbon atom.

As regards the preferred embodiments of the ligands in formulae (I), (I.1) and (I.2), they are forms in which A=B=carbon atom in the formula (II) given above.

Preferred meanings for $T_1$ and $T_2$ in this formula II are:

alkyl, in particular n-propyl, n-pentyl or neopentyl (—$CH_2$—$C(CH_3)_3$), cycloalkyl, in particular cyclopentyl, cyclohexyl or adamantyl;

alkenyl, in particular allyl (—$CH_2$—$CH{=}CH_2$), or methallyl (—$CH_2$—$C(CH_3){=}CH_2$);

alkynyl, in particular propargyl or homopropargyl (—$(CH_2)_2$—C≡CH);

or a monovalent radical (W) defined above, in particular —$(CH_2)$—C≡C—$C(CH_3)_3$ γ=1 to 3 or

—$(CH_2)$—C≡C—$Si(CH_3)_3$

γ=1 to 3

Still in formula (II) and preferably, $T_3$ and $T_4$ both correspond to hydrogen or together form an aryl, and better still a phenyl.

One group of metallic complexes of formula (I) that is particularly preferred consists of the complexes of formula:

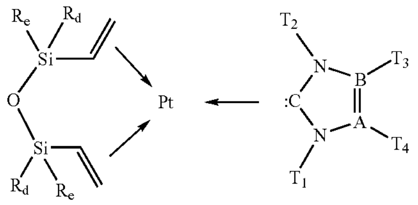

in which:

$T_1$ and $T_2$ are identical and are as defined above;

$T_3$ and $T_4$ are as defined above;

$R_d$ and $R_e$ are as defined above.

According to another of its aspects, the present invention concerns, as novel products, complexes of formula (I) in which the carbene of formula (II) is such that:

$T_3$ and $T_4$ can form, together with A and B when these each represent a carbon atom, an aryl as defined above, preferably a phenyl;

and/or $T_1$ and $T_2$ independently represent a monovalent radical of formula (V) below:

$$—V_1—V_2 \qquad (V)$$

in which:

$V_1$ is a divalent hydrocarbon-based radical, preferably an optionally substituted linear or branched $C_1$–$C_{10}$ alkylene, $V_2$ is a monovalent radical chosen from the following group of substituents:

alkoxy, —$OR^v$ with $R^v$ corresponding to hydrogen, alkyl or aryl amine, preferably $N(R^v)_2$ with $R^v$ corresponding to hydrogen, alkyl or aryl or alternatively $T_1$ and $T_2$ independently represent a monovalent radical of formula (W) below:

$$—W_1\text{-}\omega\text{-}W_2 \qquad (W)$$

in which:

$W_1$ is a divalent hydrocarbon-based radical, preferably an optionally substituted linear or branched $C_1$–$C_{10}$ alkylene, ω represents:

$$—R^{\alpha}C{=}CR^{\alpha}—$$

with $R^{\alpha}$ corresponding to H or alkyl or $-C \equiv C-$ $W_2$ is a monovalent radical chosen from the following group of substituents:

$R^{\beta}$=alkyl or H;

Si-alkyl, Si-alkenyl or Si-alkynyl, preferably $-Si(alkyl)_3$;

alcohol, preferably $-C(R^{\epsilon})_2OH$ with $R^{\epsilon}$=H or alkyl;

ketone, preferably

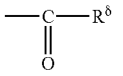

with $R^{\delta}$=alkyl; alkenyl, alkynyl;

carboxyl, preferably

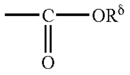

with $R^{\delta}$=alkyl; alkenyl, alkynyl;

amide, preferably

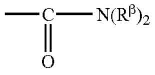

with $R^{\beta}$=H, alkyl; alkenyl, alkynyl;

acyl, preferably

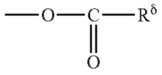

with $R^{\delta}$=alkyl; alkenyl, alkynyl;

$T_1$ and $T_2$ preferably independently corresponding to a radical W of the type $-(CH_2)-C \equiv C(CH_3)_3$ γ=1 to 3 or $-(CH_2)-C \equiv C-Si(CH_3)_3$

γ=1 to 3 or alternatively to one of the following units:

methyl, isopropyl, tert-butyl, n-pentyl, neopentyl, cyclopentyl, cyclohexyl, adamantyl, allyl, methallyl, propargyl or homopropargyl.

As regards the salt (III), the anion $Z_1^-$ is the anion derived from an organic or mineral Brönsted acid (protic acid). Usually, the anion $Z_1^-$ is derived from an acid with a pKa of less than 6. Preferably, $Z_1^-$ is derived from an acid with a pKa of less than 4 and better still less than 2. The pKa values that are concerned herein are the pKa values of the acids as measured in water.

Examples of acids are the carboxylic acids of formula: $G_o$-COOH, in which $G_o$ represents alkyl, for example $(C_1-C_{22})$alkyl; or aryl, for example $(C_6-C_{18})$aryl optionally substituted with one or more alkyl, preferably one or more $(C_1-C_6)$alkyl; sulfonic acids of formula: $G_o$-$SO_3H$ in which $G_o$ is as defined above; and phosphonic acids of formula: $G_oPO_3H$ in which $G_o$ is as defined above; other acids are HF, HCl, HBr, HI, $H_2SO_4$, $H_3PO_4$, $HClO_4$ and $HBF_4$.

Preferred examples of carboxylic acids are acetic acid, benzoic acid and stearic acid. A preferred sulfonic acid that will be mentioned is benzenesulfonic acid and a preferred phosphonic acid that will be mentioned is phenylphosphonic acid.

According to the invention, the anions $Z_1^-$ derived from acids HCl, HI and $HBF_4$ are more particularly preferred.

Thus, anions $Z_1^-$ that are particularly preferred according to the invention are the halide and tetrafluoroborate anions.

Precursor complexes (IV) that are suitable are especially complexes of formula:

$Pt_2[ViMe_2Si-O-SiMe_2Vi]_3$ (Karstedt complex)

in which Vi represents a vinyl radical; and more generally the complexes of formula:

$M_2[R_5R_6C=CR_4-Y_1-X-Y_2-CR_3=CR_1R_2]_3$ in which M, $R_5$, $R_6$, $R_4$, $R_3$, $R_1$, $R_2$, $Y_1$, X and $Y_2$ are as defined above, for instance $M_2[CR_5R_6=CR_4-SiR_dR_e-O-SiR_dR_e-CR_3=CR_1R_2]_3$, it being understood that M, $R_1$, $R_2$, $R_3$, $R_4$, $R_5$, $R_6$, $R_d$ and $R_e$ are as defined above.

As regards the solvent (V), it is chosen such that the solubility of the salt (III) and of the base (VI) in said solvent (V) is at least 0.1% weight/weight at 25° C., respectively. In point of fact, in accordance with the invention, it is preferable for the salt (III) and the base (VI) to be partially dissolved in the solvent (V).

According to one advantageous arrangement of the invention, the solvent (V) is selected from polar aprotic solvents with a boiling point at 1 atm of less than 150° C. and preferably less than 120° C., preferably from the group comprising:

cyclic or noncyclic ethers and in particular tetrahydrofuran (THF), diethyl ether, diisopropyl ether, dioxane, dimethoxyethane or diethylene glycol dimethyl ether;

dimethylformamide, dimethylacetamide, hexamethylphosphorylamide: $[(CH_3)_2N]_3PO$ and hexamethylphosphoramide $[(CH_3)_2N]_3P$ . . . ;

THF being particularly preferred.

The solvent (V) must not only provide a reaction environment that is favorable to the formation of the carbene/metal complexes, but must also be neutral and easy to remove.

As regards the base (VI), it is chosen as a function of its ability to deprotonate the salt (III) at least partially dissolved in the solvent (V).

It is preferably a strong base selected from the group comprising: alkali metal hydrides, alkali metal hydroxides, alkali metal carboxylates, alkali metal alkoxides and alkali metal amides, and even more preferably from the group comprising:

sodium hydride, sodium methoxide, potassium tert-butoxide, lithium diisopropylamide, and mixtures thereof.

According to one advantageous characteristic of the process according to the invention, the concentration of the base (VI) in the reaction medium is defined as follows [in mol/l of solvent (V)]:

$10^{-6} \leq VI \leq 10$ preferably $10^{-3} \leq VI \leq 1$.

In quantitative terms, it is important, in accordance with the invention, for the base (VI) not to be in an excess such that it results in an unwanted reaction with the constituents of the reaction medium other than the salt III to be deprotonated.

Thus, according to a noteworthy characteristic of the invention, the salt (III) and the base (VI) are used in amounts such that the ratio $R_{VI/III}$ of normality VI/III is defined as follows:

$$R_{VI/III} \leqq 10$$

preferably $1 \leqq R_{VI/III} \leqq 5$ and even more preferably $1 \leqq R_{VI/III} \leqq 3$.

These consumables III, IV, V and VI are either commercially available or are readily prepared by a person skilled in the art using commercial compounds.

A method for synthesizing the salts of formula (III) in which A=B=C is described in U.S. Pat. No. 5,077,414.

This process comprises the reaction of an α,-dicarbonyl compound of formula:

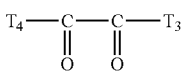

X in which $T_3$ and $T_4$ are as defined above, with HCHO and two amines of formulae $T_1$-$NH_2$ and $T_2$-$NH_2$ in the presence of a suitable acid. The nature of the anion $Z_1$ in the salts of formula III depends on the acid used in this step. The acids that may be used are, for example, those listed above and from which $Z_1$ is derived.

As regards the operating conditions, it should be noted that it is preferred to perform steps b) and c) at a temperature of between −78° C. and 50° C. and preferably at 0° C. and at atmospheric pressure.

The reaction time (steps a), b) and c)) may range, for example, from 2 hours to 48 hours. It is on average 5 hours. This time decreases as the solubility of the salt III in the medium increases. If the precursor salt is soluble in the solvent V, the reaction time may be less than one hour.

In one even more preferred embodiment of the process according to the invention, the following are used as starting materials introduced into the reaction chamber:

at least one salt (III) of formula:

($III_1$)

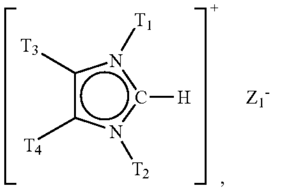

in which:

$T_1$ and $T_2$ are identical and represent $(C_1$–$C_8)$alkyl or $(C_3$–$C_8)$cycloalkyl;

$T_3$ and $T_4$ are identical and represent hydrogen or together represent a phenyl;

$Z_1$ is a halogen, preferably Cl or I, or $BF_4$;

at least one Karstedt complex (IV) as defined in U.S. Pat. No. 3,775,452, preferably a compound (IV) of formula:

(IV)

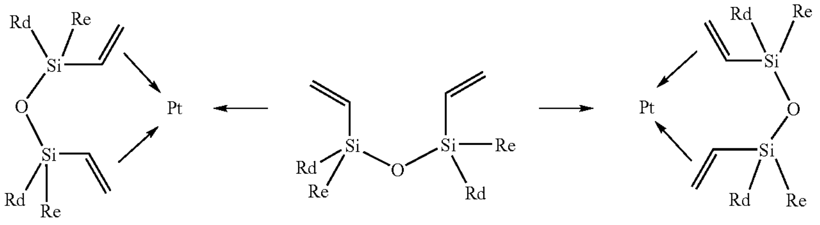

Other methods for preparing the salts of formula (III) are proposed in Chem. Eur. J. 1996, 2, No. 12, pages 1627–1636 and Angew. Chem. Int. Ed. Engl. 1997, 36, 2162–2187.

According to one preferred embodiment of the invention, the process that it concerns consists essentially in:

a) dissolving the salt (III) and the compound (IV) in the solvent (V), b) incorporating the base (VI) in several portions into the solution of (III) and (IV) in (V), c) stirring the reaction medium thus prepared until compound (I) has formed, d) recovering the formed compound (I), preferably by evaporation, e) optionally, purifying, f) optionally, drying.

in which:

Rd and Re are identical and represent $CH_3$;

a solvent (V) comprising THF, and at least one base (VI) comprising potassium tert-butoxide (KOt-Bu).

According to another of its aspects, the invention relates to a catalytic composition comprising, as active material, one or more metallic complexes prepared by performing the process according to the invention.

The catalysts thus prepared may be used in hydrosilylation reactions. They allow a homogeneous catalysis of the reaction.

A subject of the invention is thus also a hydrosilylation process and in particular for the hydrosilylation of ethylenically and/or acetylenically unsaturated compounds, characterized in that it is performed in the presence of a catalyst comprising the metallic complex obtained by the process described above.

For the purposes of the invention the expression "ethylenically and/or acetylenically unsaturated compounds" especially denotes organic compounds of the olefin or acetylenic derivative type, and also organomineral compounds, such as organosilicon compounds, for instance vinylsilicic and/or acetylsilicic derivatives.

According to the invention, the term "hydrosilylation reaction" means the reaction of a compound containing an ethylenic double bond or an acetylenic triple bond (unsaturated compound) with a compound containing at least one unit ≡Si—H so as to form a C—Si bond.

The hydrosilylation reaction may be represented schematically as follows, in the case of a compound containing an ethylenic double bond:

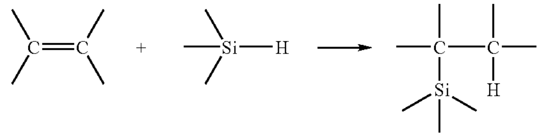

and, in the case of a compound containing an acetylenic triple bond:

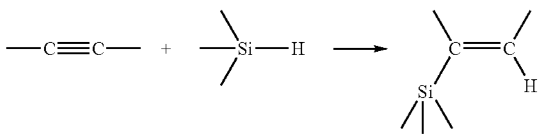

The compounds containing an ethylenic double bond may comprise one or more double bonds and from 2 to 40 carbon atoms. These compounds may be aliphatic hydrocarbons with a linear or branched hydrocarbon-based chain, or cyclic hydrocarbons, said cyclic or aliphatic hydrocarbons optionally bearing one or more substituents of $(C_6-C_{18})$aryl type optionally substituted with $(C_1-C_6)$alkyl. The double bonds are generally terminal.

Examples of olefins are 2-methyl-1-butene, 1-hexene, 1-heptene, 1-octene, 3-ethyl-1-hexene, 1-decene, 4,4-dimethyl-1-nonene, vinylcyclohexene, styrene, 2-vinylnaphthalene, and polyorganosiloxanes (POSs) comprising at least one Si-vinyl per molecule.

The compounds containing an acetylenic triple bond may comprise one or more triple bonds and from 2 to 40 carbon atoms. These compounds are generally aliphatic hydrocarbons with a linear or branched hydrocarbon-based chain, optionally substituted with $(C_3-C_{10})$cycloalkyl (which cycloalkyl may optionally bear one or more $(C_1-C_6)$alkyl) and/or with $(C_6-C_{10})$aryl (which aryl may optionally bear one or more $(C_1-C_6)$alkyl). Preferably, the compounds containing an acetylenic triple bond contain only one triple bond. The triple bonds are generally terminal. Examples of these are: 2-propynyl, 1-propynyl and 2-penten-4-ynyl.

The hydrosilylation of compounds comprising both one or more ethylenic double bonds and one or more acetylenic triple bonds may also be envisaged within the context of the invention.

Under the operating conditions normally prescribed in the literature for hydrosilylation reactions, the formation of two types of hydrosilylation reaction side products is observed, namely isomerization products and hydrogenation products. The isomerization products result from the isomerization of the double bonds. The hydrogenation products result from the hydrogenation of the double and triple bonds.

Surprisingly, when the hydrosilylation is performed using as catalysts the metallic complexes prepared by the process according to the invention, formation of these side products is greatly limited. More particularly, a strong reduction in the level of isomers formed is observed.

The hydrosilylation reaction may be performed in a solvent or in the absence of solvent. As a variant, one of the reagents may act as solvent: for example, the compound containing an ethylenic double bond or containing an acetylenic triple bond.

Suitable solvents are solvents that are miscible with the compound containing an Si—H unit.

Under the conditions of the hydrosilylation reaction, the catalytic complex should be dissolved in the reaction medium.

The compound containing an Si—H unit may be a silicon hydride of formula (XIII):

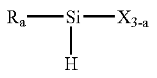

XIII in which:

X is a radical comprising a hetero atom such as O, Si, a halogen atom or the carbon atom of an aliphatic or aromatic group;

R is a hydrogen atom, an alkyl group, an aryl group, a cycloalkyl group, an alkoxy group, an aryloxy group or a cycloalkoxy group;

a is an integer from 0 to 3.

It should be understood that, according to the invention, the aliphatic, aromatic, alkyl, aryl, cycloalkyl, alkoxy, aryloxy and cycloalkoxy groups may be substituted or unsubstituted. The nature of the substituents is defined so as not to give rise to side reactions during the hydrosilylation$^{reaction}$.

Suitable examples of silanes are $HSi(OC_2H_5)_3$ and $HSi(C_2H_5)_3$.

The compound containing an Si—H unit may be a polymer of polyhydrogenosiloxane type. Other suitable polymers and copolymers are polyhydrogenosilanes comprising a large number of repeating units containing Si—H bonds.

Preferably, the polymers that may be used contain repeating units of formula:

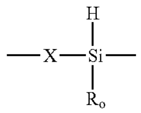

in which X is a radical comprising a hetero atom such as O, Si or the carbon atom of an aliphatic or aromatic group; and $R_o$ is a hydrogen atom or an organic group chosen from alkyl, aryl, cycloalkyl, alkoxy, aryloxy or cycloalkoxy. Examples that may be mentioned include the polyhydrogenosiloxanes of formula:

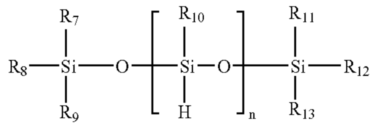

in which $R_7$ to $R_{13}$ are independently a hydrogen atom or an organic group. Preferably, $R_7$, $R_8$, $R_9$, $R_{10}$, $R_{11}$, $R_{12}$ and $R_{13}$ are chosen from a hydrogen atom and an alkyl, aryl, cycloalkyl, alkoxy, aryloxy or cycloalkoxy group;

n is an integer at least equal to 1, preferably at least equal to 10 and better still between 10 and 100.

Suitable polymers are polymethylhydrogenosiloxanes containing $—Si(CH_3)_3$ end groups and polydimethylsiloxanes containing $—Si(CH_3)_2H$ end groups, methylhydrogenodimethylsiloxane copolymers containing $—Si(CH_3)_2H$ end groups, methylhydrogenomethyloctylsiloxane copolymers and methylhydrogenocyclosiloxane polymers.

In general, the polymers that may be used in the reaction have an average molecular mass of 300 or more and preferably between 300 and 10 000 (g/mol).

Examples of silicon hydrides are described in U.S. Pat. No. 5,359,113.

Examples of solvents that may be used for the hydrosilylation are especially aliphatic hydrocarbons (such as pentane, hexane, heptane, pentamethylheptane or petroleum distillation fractions); aromatic hydrocarbons (such as benzene, toluene and xylenes: ortho-xylene, para-xylene and meta-xylene); halogenated aliphatic or aromatic hydrocarbons (such as tetrachloroethylene); or ethers (such as tetrahydrofuran or dioxane).

The hydrosilylation reaction may be performed at a temperature of between 15° C. and 300° C., for example between 20 and 240° C., better still between 70 and 200° C., especially between 50 and 140° C. and very preferably between 50 and 100° C.

The relative amount of unsaturated compound and of compound containing an Si—H unit may be controlled so as to ensure the reaction of all the unsaturations with Si—H bonds.

Nevertheless, it is preferable to work in the presence of a molar excess of unsaturation.

Generally, the molar ratio of the unsaturations to the Si—H bonds ranges between 1:100 and 10:1.

According to the invention, the hydrosilylation reaction is performed in the presence of a catalytic amount of one or more complexes prepared according to the invention. The term "catalytic amount" means less than one molar equivalent of platinum relative to the amount of unsaturations present in the reaction medium.

In general, it suffices to introduce into the reaction medium less than 1000 ppm, preferably less than 100 ppm and better still less than 50 ppm of platinum, calculated relative to the total mass of the unsaturated compound and of the compound containing Si—H units.

According to one preferred embodiment of the invention, the unsaturated compound, the catalyst and the solvent are stirred in a reactor. The mixture is brought to the desired temperature and the compound containing Si—H units is introduced with stirring.

The invention is illustrated in the light of the examples that follow.

EXAMPLES

General Features

The synthesis starting with the Karstedt complex (IV) is summarized in the scheme below:

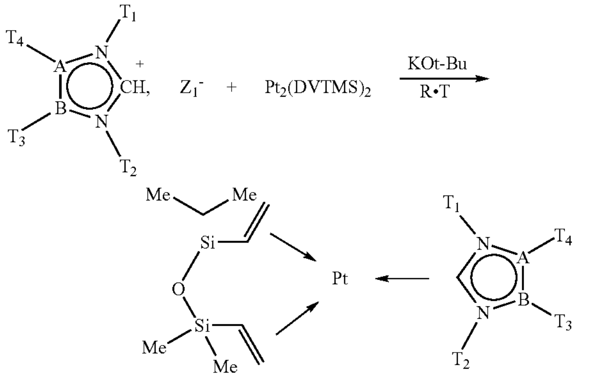

A, B, $T_1$, $T_2$, $T_3$, $T_4$ and $Z_1$ being as defined above;

DVTMS=divinyltetramethylsiloxane

KOt-Bu=potassium tert-butoxide

RT=room temperature

The imidazolium salt is placed in contact with the platinum complex in THF. The addition of a strong base (potassium tert-butoxide) to the reaction mixture allows the formation of the carbene, which exchanges rapidly with one of the olefins complexed to the metal to give the corresponding platinum-carbene.

The reaction yields and selectivity are good. In addition, this process is advantageous as a result of its ease of implementation.

Example 1

| | |
|---|---|
| Scale: | 1.8 mmol |
| Glassware: | 200 ml round-bottomed flask<br>Magnetic stirring |

Additions:

4.97 grams of a Karstedt solution containing 16.1% of platinum, i.e. 4.1 mmol of platinum, 1.31 g of N,N-di(cyclohexyl)imidazolium tetrafluoroborate, i.e. 4.1 mmol (A=B=C; $T_3$=$T_4$=H, $T_1$=$T_3$=cyclohexyl), prepared according to the method described in Chem. Eur. J. 1996, 2, No. 12, pages 1627–1636 and Angew. Chem. Int. Ed. Engl. 1997, 36, 2162–2187, 926 mg of potassium tert-butoxide, i.e. 8.2 mmol (2 equiv.), 100 mL of dry THF.

The solution of Karstedt complex and the imidazolium salt are dissolved in the THF. The potassium tert-butoxide is added over one hour at 0° C. and the mixture is stirred for five hours. The reaction medium is concentrated under vacuum. The residue is taken up in 30 ml of dichloromethane. This organic phase is then washed with three times 20 ml of water and then twice 20 ml of saturated $NaHCO_3$ solution. The organic phase is recovered and then concentrated under vacuum. The solid residue is then washed with three times 2 ml of ethanol. 1.8 g of an analytically pure white solid are thus obtained (71% yield).

Example 2

| | |
|---|---|
| Scale: | 1.0 mmol |
| Glassware: | 100 ml round-bottomed flask |
| | Magnetic stirring |

Additions:

1.20 grams of a Karstedt solution containing 16.2% platinum, i.e. 1 mmol of platinum, 268 mg of N,N-di(t-butyl)imidazolium tetrafluoroborate, i.e. 1 mmol (1.0 equiv.) (A=B=C; $T_3$=$T_4$=H, $T_1$=$T_2$=t-butyl), 240 mg of potassium tert-butoxide, i.e. 2 mmol (2 equiv.), 80 ml of dry THF.

The solution of the Karstedt complex and the imidazolium salt are diluted in 80 ml of THF. The potassium tert-butoxide is added at room temperature and the mixture is stirred for 10 hours in the absence of light. The reaction medium is evaporated and the solid obtained is purified by rapid filtration through silica gel (eluent: $H_2Cl_2$). After evaporating off the solvent, the mixture is rinsed with two milliliters of hexamethyldisiloxane and then dried under vacuum. 640 mg of an analytically pure white solid are obtained (98% yield).

Example 3

| | |
|---|---|
| Scale: | 0.5 mmol |
| Glassware: | 50 ml round-bottomed flask |
| | Magnetic stirring |

Additions:

0.6 gram of a Karstedt solution containing 16.2% platinum, i.e. 0.5 mmol of platinum, 137 mg of N,N-dimethylbenzimidazolium iodide, i.e. 0.5 mmol (1. 0 equiv.) (A,B,$T_3$,$T_4$=benzyl; $T_1$=$T_2$=methyl), 112 mg of potassium tert-butoxide, i.e. 1 mmol (2 equiv.)

20 ml of dry THF.

The solution of the Karstedt complex and the benzimidazolium salt are placed in the round-bottomed flask and then diluted in 20 ml of THF. The potassium tert-butoxide is added at room temperature and the mixture is stirred for 36 hours in the absence of light. The reaction medium is diluted in dichloromethane and then washed with water. The solvent is evaporated off and the oil obtained is rapidly filtered through silica gel (eluent: $CH_2Cl_2$). After evaporating off the solvent, the solid obtained is rinsed with two milliliters of hexamethyldisiloxane. 173 mg (66% yield) of an analytically pure white solid are obtained.

The invention claimed is:

1. A process for preparing metallic complexes of formula (I):

I

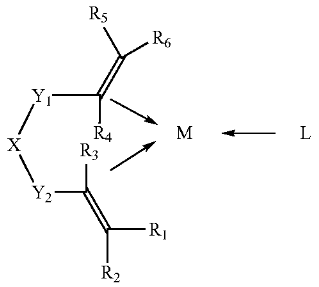

in which:

M represents a metal selected from the metals of group 8 of the Periodic Table as published in the Handbook of Chemistry and Physics, 65th Edition, 1984–1985;

X represents O, $NR_a$ or $CR_fR_g$;

$Y_1$ and $Y_2$ represent, independently of each other, $CR_bR_c$ or $SiR_dR_e$;

$R_1$, $R_2$, $R_3$, $R_4$, $R_5$, $R_6$, $R_a$, $R_b$ and $R_c$, which may be identical or different, are selected from a hydrogen atom; an alkyl group; an acyl group; an aryl group optionally substituted with alkyl; a cycloalkyl group optionally substituted with alkyl; and an arylalkyl group in which the aryl portion is optionally substituted with alkyl;

$R_d$ and $R_e$ are independently chosen from alkyl; aryl optionally substituted with alkyl; cycloalkyl optionally substituted with alkyl; and arylalkyl in which the aryl portion is optionally substituted with alkyl; or alternatively when $Y_1$ and $Y_2$ independently represent $SiR_dR_e$, two groups $R_d$ linked to two separate silicon atoms together form a chain of formula:

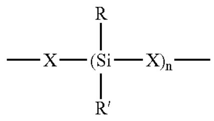

in which n is an integer from 1 to 3; X is as defined above; R and R', which may be identical or different, take any of the meanings given above for $R_e$, it being understood that, when n is 2 or 3, only one silicon atom of said chain may be substituted with one or two alkenyl or alkynyl groups; or alternatively when $Y_1$ and $Y_2$ independently represent $SiR_d R_e$, two groups $R_d$ linked to separate silicon atoms together form a saturated hydrocarbon-based chain, the two groups $R_d$ together with said silicon atoms and X forming a 6- to 10-membered ring; or alternatively when $Y_1$ and $Y_2$ independently represent $CR_bR_c$, two groups $R_b$ linked to separate carbon atoms together form a saturated hydrocarbon-based chain, the two groups $R_b$ together with the carbon atoms that bear them and X form a 6- to 10-membered ring; and $R_f$ and $R_g$ represent, independently of each other, a hydrogen atom; an alkyl group; an acyl group; an aryl group optionally substituted with alkyl; a cycloalkyl group optionally substituted with alkyl; an arylalkyl group in which the aryl portion is optionally substituted with alkyl; a halogen atom; an alkenyl group; an alkynyl group; or a group $SiG_1G_2G_3$ in which $G_1$, $G_2$ and $G_3$ are; independently of each other, alkyl; alkoxy; aryl optionally substituted with alkyl or alkoxy; or arylalkyl in which the aryl portion is optionally substituted with alkyl or alkoxy;

L represents a carbene of formula (II):

(II)

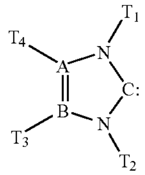

in which:

A and B independently represent C or N, it being understood that when A represents N, then $T_4$ represents nothing, and when B represents N, then $T_3$ represents nothing;

$T_3$ and $T_4$ independently represent a hydrogen atom; an alkyl group; a cycloalkyl group optionally substituted with alkyl or alkoxy; an aryl group optionally substituted with alkyl or alkoxy; an alkenyl group; an alkynyl group; or an arylalkyl group in which the aryl portion is optionally substituted with alkyl or alkoxy; or alternatively $T_3$ and $T_4$ may form, together with A and B when these each represent a carbon atom, an aryl;

$T_1$ and $T_2$ independently represent an alkyl group; an alkyl group optionally substituted with alkyl; a perfluoroalkyl group or an alkyl group optionally substituted with a perfluoroalkyl group; a cycloalkyl group optionally substituted with alkyl or alkoxy; an aryl group optionally substituted with alkyl or alkoxy; an alkenyl group; an alkynyl group; or an arylalkyl group in which the aryl portion is optionally substituted with alkyl or alkoxy; or alternatively $T_1$ and $T_2$ independently represent a monovalent radical of formula (V) below:

$$—V_1—V_2 \quad (V)$$

in which:

$V_1$ is a divalent hydrocarbon-based radical, optionally substituted linear or branched $C_1$–$C_{10}$ alkylene, $V_2$ is a monovalent radical chosen from the following group of substituents:

alkoxy, $—OR^{\nu}$ with $R^{\nu}$ corresponding to hydrogen, alkyl or aryl amine, preferably $N(R^{\nu})_2$ with $R^{\nu}$ corresponding to hydrogen, alkyl or aryl, or alternatively $T_1$ and $T_2$ independently represent a monovalent radical of formula (W) below:

$$—W_1—\omega—W_2 \quad (W)$$

in which:

$W_1$ is a divalent hydrocarbon-based radical, preferably an optionally substituted linear or branched $C_1$–$C_{10}$ alkylene, ω to represents:

$$—R^{\alpha}C{=}CR^{\alpha}—$$

with $R_{\alpha}$ corresponding to H or alkyl or $$—C{\equiv}C—$$

$W_2$ is a monovalent radical selected from the following group of substituents:

$R^{\beta}$=alkyl, H;

Si-alkyl, Si-alkenyl or Si-alkynyl, preferably Si-$(alkyl)_3$;

alcohol, preferably $—C(R^{\epsilon})_2OH$ with $R^{\epsilon}$=OH, H or alkyl;

ketone, preferably

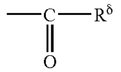

with $R^{\delta}$=alkyl; alkenyl, alkynyl;

carboxyl, preferably

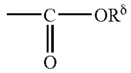

with $R^{\delta}$=alkyl; alkenyl, alkynyl;

amide, preferably

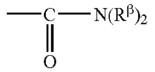

with $R^{\beta}$=H, alkyl; alkenyl, alkynyl;

acyl, preferably

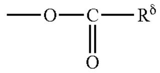

with $R^{\delta}$=alkyl; alkenyl, alkynyl;

or alternatively the substituents $T_1$, $T_2$, $T_3$ and $T_4$ can form in pairs, when they are located on two adjacent ring members in formula II, a saturated or unsaturated hydrocarbon-based chain;

this process comprising placing in contact:

at least one salt of formula (III):

(III)

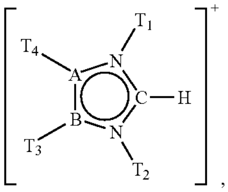 $Z_1^-$ , in which:

A, B, $T_1$, $T_2$, $T_3$ and $T_4$ are as defined above;

$Z_1$ independently represents an anion derived from a Brönsted acid (protic acid) selected from the group comprising:

carboxylic acids of formula Go-COOH in which Go represents an alkyl, and optionally a $C_1$–$C_{22}$ alkyl; an aryl, optionally a $C_6$–$C_{18}$ aryl optionally substituted with one or more $C_1$–$C_6$ alkyls;

sulfonic acids of formula Go-$SO_3H$ in which Go is as defined above;

phosphoric acids of formula Go-$PO_3H$ in which Go is as defined above;

the following mineral acids: HF, HCl, HBr, HI, $H_2SO_4$, $H_3PO_4$, $HClO_4$ and $HBF_4$ taken individually or in combination;

and mixtures thereof;

at least one precursor complex (IV) selected from the group of suitable complexes comprising the complexes of formula:

$Pt_2[ViMe_2Si—O—SiMe_2Vi]_3$ (Karstedt complex) in which Vi represents a vinyl radical; and more generally the complexes of formula:

$$M_2[R_5R_6C{=}CR_4—Y_1—X—Y_2—CR_3{=}CR_1R_2]_3$$

in which M, $R_5$, $R_6$, $R_4$, $R_3$, $R_1$, $R_2$, $Y_1$, X and $Y_2$ are as defined above, for instance: $M_2[CR_5R_6{=}CR_4—SiR_dR_e—O—SiR_dR_e—CR_3{=}CR_1R_2]_3$, it being understood that M, $R_1$, $R_2$, $R_3$, $R_4$, $R_5$, $R_6$ and $R_e$ are as defined above;

at least one solvent (V), and at least one base (VI).

2. The process as claimed in claim 1, wherein the compound of formula (I) is obtained in a single step.

3. The process as claimed in claim 1, wherein the solvent (V) is chosen such that the solubility of the salt (III) and of the base (VI) in said solvent (V) is at least 0.1% weight/weight at 25° C., respectively.

4. The process as claimed in claim 1, wherein the solvent (V) is selected from polar aprotic solvents with a boiling point at 1 atm of less than 150° C. comprising:

cyclic or noncyclic ethers and in particular tetrahydrofuran (THF), diethyl ether, diisopropyl ether, dioxane, dimethoxyethane or diethylene glycol dimethyl ether;

dimethylformaxnide, dimethylacetamide, hexamethylphosphorylamide: $[(CH_3)_2N]_3PO$ and hexamethylphosphoramide $[(CH_3)_2N]_3P$.

5. The process as claimed in claim 1, wherein the base(s) (VI) is (are) selected from strong bases capable of deprotonating the salt (III) from the group comprising:

alkali metal hydrides, alkali metal hydroxides, alkali metal carboxylates, alkali metal alkoxides and alkali metal amides, and even more preferably from the group comprising:

sodium hydride, sodium methoxide, potassium tertbutoxide, lithium diisopropylamide, and mixtures thereof.

6. The process as claimed in claim 1, wherein the concentration of the base (VI) in the reaction medium, in M/1 of solvent (V), is:

$$10^{-6} \leqq VI \leqq 10.$$

7. The process as claimed in claim 1, wherein the salt (III) and the base (VI) are used in amounts such that the ratio $R_{VI/III}$ of normality VI/III is defined as follows:

$$R_{VI/III} \leqq 10.$$

8. The process as claimed in claim 1, comprising:

a) dissolving the salt (III) and the compound (IV) in the solvent (V), b) incorporating the base (VI) in several portions into the solution of (III) and (IV) in (V), c) stirring the reaction medium thus prepared until compound (I) has formed, d) recovering the formed compound (I), preferably by evaporation, e) purifying, f) drying.

9. The process as claimed in claim 1, wherein steps b) and c) are performed at a temperature of between −78° C. and 50° C.

10. The process as claimed in claim 1, wherein the following are used:

at least one salt (III) of formula:

(III$_1$)

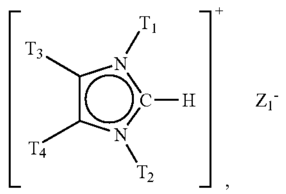

in which:

$T_1$ and $T_2$ are identical and represent ($C_1$–$C_8$)alkyl or ($C_3$–$C_8$) cycloalkyl;

$T_3$ and $T_4$ are identical and represent hydrogen or together represent a phenyl;

$Z_1$ is a halogen;

at least one Karstedt complex (IV), optionally a compound (IV) of formula:

(IV)

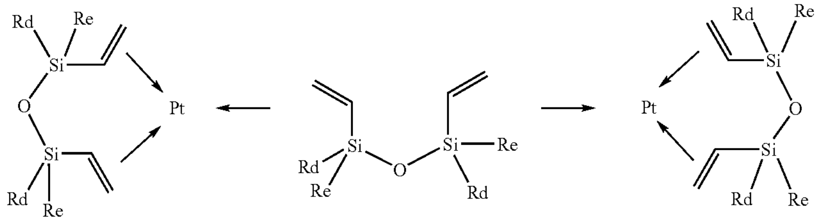

in which:

Rd and Re are identical and represent $CH_3$;

a solvent (V) comprising THF, and at least one base (VI) comprising potassium tertbutoxide (KOt-Bu).

11. A process for the hydrosilylation of ethylenically and/or acetylenically unsaturated compounds, which is performed in the presence of a catalyst comprising the metallic complex obtained by the process as claimed in claim 1.

* * * * *